US008160672B2

(12) United States Patent
Kim et al.

(10) Patent No.: US 8,160,672 B2
(45) Date of Patent: Apr. 17, 2012

(54) METHOD AND SYSTEM FOR DATA COMMUNICATION IN HUMAN BODY AND SENSOR THEREFOR

(75) Inventors: Tae-Song Kim, Seoul (KR); Jong-Oh Park, Seoul (KR); Byung-Kyu Kim, Seoul (KR); Jin-Seok Kim, Seoul (KR); Han Cheung, Daejeon (KR); Won-Woo Cho, Daejeon (KR); Nan-Young Yoon, Daejeon (KR); Young-Rok Kim, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 1187 days.

(21) Appl. No.: 10/543,143

(22) PCT Filed: Dec. 31, 2003

(86) PCT No.: PCT/KR03/02937
§ 371 (c)(1),
(2), (4) Date: Jul. 22, 2005

(87) PCT Pub. No.: WO2004/068748
PCT Pub. Date: Aug. 12, 2004

(65) Prior Publication Data
US 2006/0243288 A1    Nov. 2, 2006

(30) Foreign Application Priority Data

Jan. 25, 2003  (KR) .................. 10-2003-0005059

(51) Int. Cl.
*A61B 5/04* (2006.01)
(52) U.S. Cl. ........... 600/380; 600/373; 128/899; 607/60
(58) Field of Classification Search .............. 607/59–61, 607/115, 148; 606/35; 128/899; 600/372–385, 600/424, 431
See application file for complete search history.

(56) References Cited

U.S. PATENT DOCUMENTS 4,267,415 A * 5/1981 Holmes et al. ................ 218/139
4,628,934 A * 12/1986 Pohndorf et al. ............... 607/27
(Continued)

FOREIGN PATENT DOCUMENTS
EP        0109184 A2    5/1984
(Continued)

OTHER PUBLICATIONS

Laks, M. M. et al., Recommendations for safe current limits for electrocardiographs: a statement from the committee on electrocardiography, american heart association, 1996;93:837-839.*
(Continued)

*Primary Examiner* — John P Leubecker
*Assistant Examiner* — Christopher Sponheimer
(74) *Attorney, Agent, or Firm* — NSIP Law

(57) ABSTRACT

The present invention provides method and system for data communication in the human body and a sensor therefor. The method and system transmit information through the human body to a receiver located outside the human body using low current and voltage polarity, so that they cause no damage to the human body and achieve low power consumption and better receiving sensitivity. In addition, the sensor contains a CMOS image sensor on which all circuits are integrated without radio transmitter and antenna, so that it achieves a low-priced and small-sized capsule type endoscope.

21 Claims, 3 Drawing Sheets

U.S. PATENT DOCUMENTS

| | | | |
|---|---|---|---|
| 5,111,816 A * | 5/1992 | Pless et al. ............... 607/4 |
| 5,146,920 A * | 9/1992 | Yuuchi et al. ............. 607/63 |
| 5,337,230 A * | 8/1994 | Baumgartner et al. ....... 700/9 |
| 5,651,869 A * | 7/1997 | Yoshioka et al. ....... 204/403.12 |
| 5,796,827 A * | 8/1998 | Coppersmith et al. ....... 713/182 |
| 5,811,897 A | 9/1998 | Spaude et al. |
| 5,833,603 A | 11/1998 | Kovacs et al. |
| 5,914,701 A | 6/1999 | Gersheneld et al. ......... 345/156 |
| 6,104,913 A * | 8/2000 | McAllister ................. 455/41.1 |
| 6,165,178 A * | 12/2000 | Bashiri et al. ............... 606/108 |
| 6,223,018 B1 * | 4/2001 | Fukumoto et al. .......... 455/41.1 |
| 6,409,674 B1 * | 6/2002 | Brockway et al. ........... 600/486 |
| 6,771,161 B1 * | 8/2004 | Doi et al. .................... 340/5.64 |
| 7,425,202 B2 * | 9/2008 | Huang et al. ................ 600/564 |
| 7,463,918 B2 * | 12/2008 | Kim et al. ................... 600/407 |
| 2002/0138009 A1 | 9/2002 | Brockway et al. |
| 2003/0040291 A1 * | 2/2003 | Brewer ....................... 455/127 |
| 2003/0092973 A1 | 5/2003 | Kim et al. |
| 2006/0173265 A1 * | 8/2006 | Kim et al. ................... 600/407 |

FOREIGN PATENT DOCUMENTS

| | | |
|---|---|---|
| EP | 0 667 115 A1 | 1/1995 |
| GB | 2308481 A | 6/1997 |
| JP | 57-160436 A | 10/1982 |
| JP | 60-250731 A | 12/1985 |
| JP | 08-084779 A | 4/1996 |
| JP | 2001-245844 A | 9/2001 |

OTHER PUBLICATIONS

Search Report issued by European Patent Office on Aug. 4, 2006 in connection with corresponding European patent application No. EP 03 78 1095.

*Micro-Transponder Systems for Medical Applications*, Mokwa, et. al., *IEEE Transactions*, vol. 50, No. 6, pp. 1551-1555, Dec. 2001, XP11025449.

*Development and Performance Analysis of an Intra-Body Communication Device*, Hachisuka, et. al., *IEEE*, vol. 2, Jun. 2003, pp. 1722-1725, XP010547499.

*A Real-time Fault Tolerant Intra-body Network*, Baskiyar, et. al., *IEEE Conference*, Nov. 2002, pp. 235-240, XP010628172.

International Search PCT/2003/002937 dated Feb. 25, 2004.

Chinese Office Action issued on Apr. 28, 2010, in corresponding Chinese Application No. 200380109156.3 (12 pages).

* cited by examiner

METHOD AND SYSTEM FOR DATA COMMUNICATION IN HUMAN BODY AND SENSOR THEREFOR

CROSS REFERENCE TO RELATED APPLICATION

The present application is a 35 U.S.C. §371 national phase conversion of PCT/KR2003/002937 filed 31 Dec. 2003, which claims priority of Korean Patent Application No. 10-2003-0005059 filed 25 Jan. 2003.

TECHNICAL FIELD

The present invention relates to a method and system for transmitting data from a sensor put in the human body to the outside of the human body to collect various medical information, and particularly to a method and system for data communication in human body, wherein a current generated from the sensor flows through the human body as a conductor to transmit data to the outside of the human body.

BACKGROUND ART

Various sensors for collecting medical information in the human body have been developed and used, herein, not only a technique for collecting information in the human body but also a technique for transmitting collected information to the outside of the human body are very important.

In general data transmitting methods, there is a communication cable method applied to an endoscope which is developed for observing the stomach and intestines. In the communication cable method, a cable made of a conducting wire or an optic fiber is inserted into the human body through throat of the patient. The communication cable method has high reliability and high data quality, however, it may cause severe pain to the patient.

In order to solve the above-mentioned problem, Given Imaging LTD. in Israel has developed a capsule type endoscope called M2A. When a patient swallows the capsule type endoscope like a tablet, video data in the human body photographed by a camera of the endoscope are transmitted to an external-receiving unit, and displayed in a monitor.

However, in the capsule type endoscope, since radio wave is used to transmit a signal, power consumption is large, so that operation time is short, and receiving sensitivity is deteriorated due to interference of various electric waves from the outside of the human body. In addition, radio-transmitting apparatus such as a converter circuit for converting a video signal into a high frequency signal and an antenna for signal transmission, etc. are required, so that volume is increased and production cost is increased. Also, high frequency may be harmful to the human body.

SUMMARY OF THE INVENTION

In order to solve the above-described problems, it is an object of the present invention to provide a method and system for data communication in the human for flowing a current generated from the sensor through the human body to transmit data to the outside of the human body.

In addition, it is another object of the present invention to provide a sensor having a transmitting electrode capable of generating a current in the human body to flow a current through the human body to transmit data to the outside of the human body.

In order to achieve the above-mentioned objects, in a method for transmitting a signal from a sensor put in the human body to the outside of the human body, a method for data communication in the human body in accordance with the present invention includes the steps of generating electric potential difference between transmitting electrodes installed on the surface of the sensor; supplying a current from the transmitting electrode having higher electric potential to the inside of the human body to flow the current through the surface of the human body back into the inside of the human body and sinking the current to the transmitting electrode having lower electric potential; and inducing a voltage between receiving electrodes installed on the surface of the human body by the current flowing through the surface of the human body.

In addition, a system for data communication in the human body in accordance with the present invention includes a sensor, which is put in the human body, having transmitting electrodes for generating electric potential difference; and a receiver installed on the surface of the human body for receiving a current generated by the electric potential difference through the human body.

In addition, a sensor in accordance with the present invention includes a lighting device for irradiating the inside of the human body; a lens for focusing light incident from the inside of the human body; a CMOS image sensor for generating an electric signal from the light focused by the lens; a housing for containing the lighting device, the lens and the CMOS image sensor; and a transmitting electrode installed on the surface of the housing to receive the electric signal.

BRIEF DESCRIPTION OF DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Hereinafter, the preferred embodiment of the present invention will be described with reference to accompanying drawings.

Figure 1:
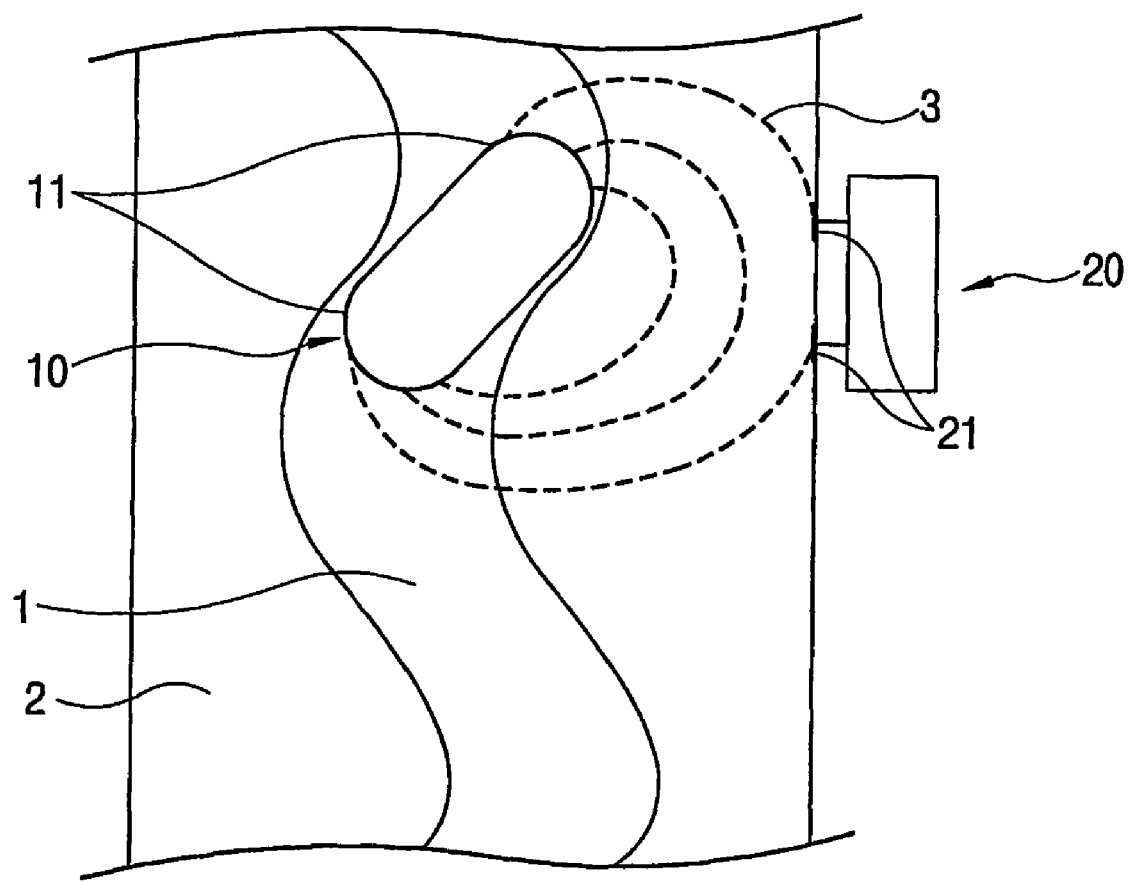
FIG. 1 is an exemplary view illustrating a method for data communication in the human body in accordance with the present invention.
Figure 2A:
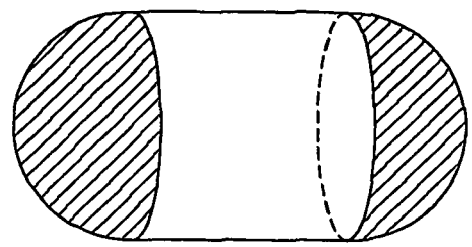
FIG. 2 are perspective views illustrating several embodiments of a transmitting electrode installed to the surface of a sensor used in a system for data communication in the human body in accordance with the present invention.
Figure 2B:
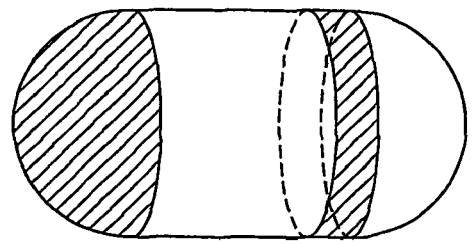
Figure 2C:
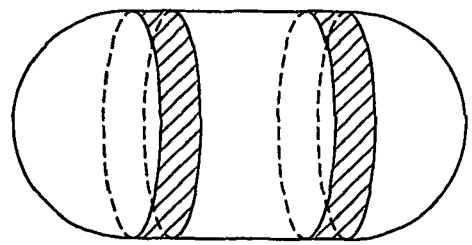
Figure 2D:
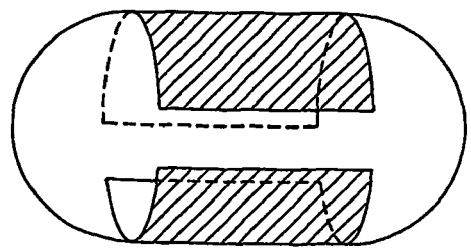

FIG. 1 is an exemplary view illustrating a method and a system for data communication in the human body in accordance with the present invention. As depicted in FIG. 1, a sensor 10 placed inside the human body 1, for example, in the digestive organs transmits information of the inside of the human body 1 to a receiver 20 installed on the surface of the human body through the human body 2.

With reference to FIG. 1, in the system for data communication in the human body in accordance with the present invention, a method for data communication in the human body capable of transmitting a signal from the sensor 10 inside the human body 1 to the receiver 20 placed in the outside of the human body will be described in more detail. Various information (for example, pictures of the inside of the body, PH, temperature or electric impedance, etc.) collected by the sensor 10 is converted into an electric signal by a signal processing circuit of the sensor and is applied to a transmitting electrode 11 through an output line of the signal processing circuit, and accordingly electric potential difference occurs between the two transmitting electrodes 11. Because the transmitting electrode 11 is contacted to the inside of the human body 1 (it is electrically connected with the human body through body fluids in the digestive organs), by electric potential difference between the two transmitting electrodes 11, a current 3 flows through the human body 2. The current 3 flows from the transmitting electrode having higher electric potential through the surface of the human body back into the inside of the human body 1 and is sunken to the transmitting electrode having lower electric potential. Herein, the current flowing through the surface of the human body induces a voltage between two receiving electrodes 21, a signal transmitted from the sensor 10 put in the human body 1 can be sensed by the receiver 20 outside of the human body. The receiver 20 restores a video signal by processing the received signal, displays it on a monitor or stores it in a memory.

FIG. 2 illustrate several embodiments of the transmitting electrode 11 installed on the surface of the sensor 10 of the system for data communication in the human body in accordance with the present invention. On the surface of the sensor 10, two metal plates, namely, two transmitting electrodes are formed, which are respectively connected to outlines of a signal processing circuit of the sensor.

If the two transmitting electrodes are electrically isolated and separated from each other sufficiently, the transmitting electrodes can be formed at any position of the surface of the sensor. Herein, it is preferable that the transmitting electrodes have a sensor-covering shape, namely, a three-dimensionally curved shape in order to be contacted with the inside of the human body easily.

In FIG. 2, (a) shows a structure of the transmitting electrode of sensor shown in FIG. 1. The transmitting electrode consists of a first electrode and a second electrode respectively surrounding the both ends of the sensor. A transmitting electrode shown in (b) consists of a first electrode surrounding an end of the sensor and a second electrode covering the other end of the sensor as a band shape. A transmitting electrode shown in (c) consists of a first electrode and a second electrode respectively covering both ends of the sensor as a band shape. In addition, a transmitting electrode shown in (d) consists of a first electrode and a second electrode symmetrically formed along a longer axis of the sensor.

Because the transmitting electrode is exposed to the inside of the human body, it has to be made of metal having good resistance against corrosion by a reactive material such as a digestive fluid, etc. and also harmless to the human body. In the embodiments of the present invention, as metal having good corrosion resistance and harmless to the human body, SUS316L or gold is used. In addition, in order to isolate the transmitting electrodes formed on the surface of the sensor electrically, the surface of the sensor has to be a nonconductor harmless to the human body. As a nonconductor harmless to the human body, peek, polyethylene or polypropylene in a plastic group may be used. In order to improve harmlessness to the human body, parylene may be coated onto the surface of the sensor made of peek, polyethylene or polypropylene.

Figure 3:
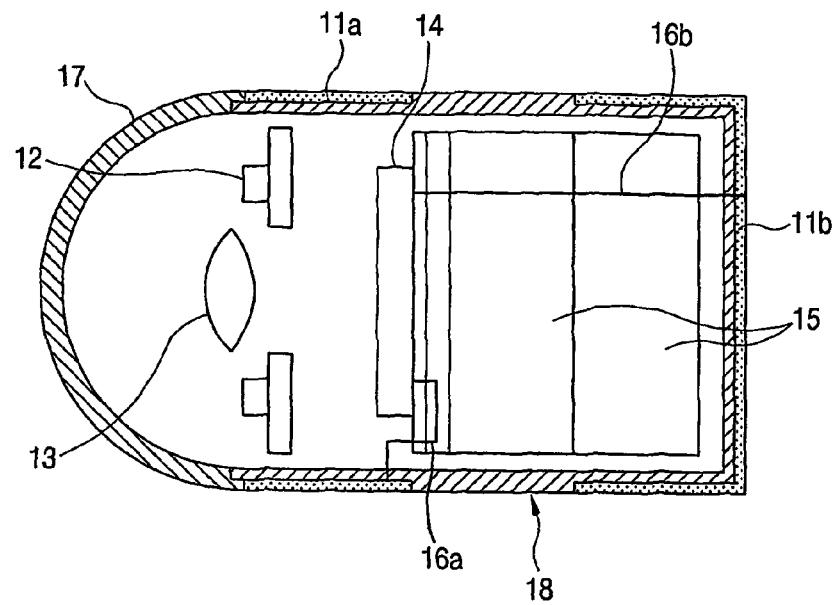
FIG. 3 is a sectional view illustrating the sensor of the system for data communication in the human body in accordance with the present invention.

FIG. 3 is a sectional view illustrating an internal structure of a capsule type endoscope as a sensor used for the system in accordance with the present invention. As depicted in FIG. 3, the capsule type endoscope has a diameter of 10 mm and a length of 20 mm. A light receiving window 17 of dome shape is formed in an end of a housing forming an external shape of the capsule type endoscope, and a rectangular container 18 is formed in the other end of the housing. Accordingly, the capsule type endoscope has a bullet shape.

In the capsule type endoscope, the light receiving window 17 which is a part for passing light is made of a nonconductor harmless to the human body and passing light. The container 18 that is a part for containing several devices also is made of a nonconductor harmless to the human body. The light receiving window 17 and the container 18 are sealed so that infiltration of a digestive fluid, etc. into the capsule type endoscope may be prevented and also leakage of substances in the capsule type endoscope into the human body may be avoided.

As depicted in FIG. 3, the capsule type endoscope has the external shape of the housing consisting of the light receiving window 17 and the container 18. The container 18 includes a lighting device 12, a lens 13, a CMOS image sensor 14 and a battery 15 and a transmitting electrode 11 electrically isolated-formed on the surface of the container 18.

First, the lens 13 is arranged behind the light receiving window 17, and the CMOS image sensor 14 in which various circuits are integrated is arranged behind the lens 13. A distance between the lens 13 and the CMOS image sensor 14 is adjusted so as to focus light incident through the light receiving window 17 on the surface of the CMOS image sensor 14. Around the lens 13 and the CMOS image sensor 14, plural lighting devices 12 are arranged as donut-shape. In the embodiment of the present invention, four LEDs are used for the lighting devices 12. Non-reflection coating is performed on the inner and outer surfaces of the light receiving window 17 so that light irradiated from the lighting device 12 may pass through the light receiving window 17 smoothly and illuminate an object. A battery 15 as power supply is arranged behind the CMOS image sensor 14. In the embodiment of the present invention, a silver oxide battery having an even discharge voltage and causing little harm to the human body is used as the battery 15.

The operation of the capsule type endoscope will be described. While the lighting devices 12 irradiate a light, the CMOS image sensor 14 captures an image of the object through the lens 13. The CMOS image sensor 14 processes the captured video signal through various internal circuits and applies the signal to the transmitting electrodes respectively connected to the two output lines 16, and accordingly the receiving electrode placed in the outside of the human body can sense the signal, as described above.

Figure 4:
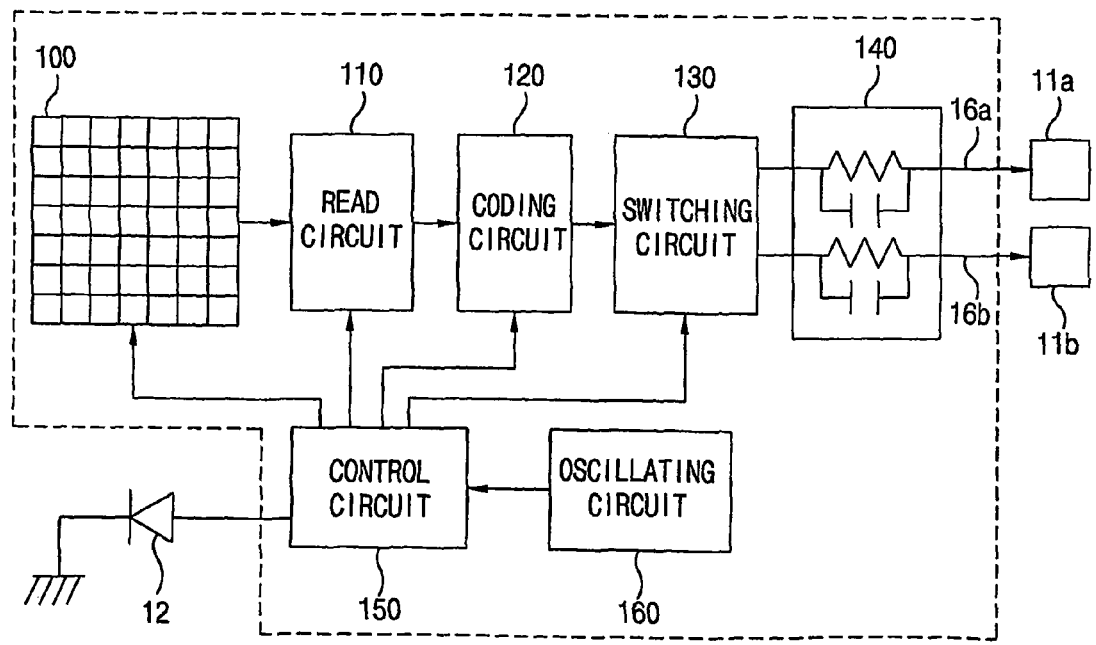
FIG. 4 is a circuit diagram illustrating an internal construction of a CMOS image sensor of the sensor.

FIG. 4 is a circuit diagram illustrating the CMOS image sensor 14 in order to describe the operation principles of the capsule type endoscope in more detail.

As depicted in FIG. 4, the CMOS image sensor 14 includes a pixel array 100 for capturing and storing a video signal; a read circuit 110 for fetching a signal of each pixel sequentially; a coding circuit 120 for coding an output signal of the read circuit 110; a switching circuit 130 for transmitting a signal coded in the coding circuit 120 through the two output lines; a current limiting circuit 140 for adjusting a current value so as to prevent flowing of a current causing damage to the human body; a control circuit 150 for controlling the signal processing and the operation of the lighting device 12; and an oscillating circuit 160 for determining an operational frequency.

In the embodiment of the present invention, the pixel array 100 (of 320×240 pixels) can capture and store video signals of high resolution. The read circuit 110 processes the stored video signals sequentially as a frame or more per 1 sec, and accordingly there is no need to have a memory disadvantageous in the cost and volume aspects. In addition, the control circuit 150 determines brightness inside the human body based on brightness of light incident to the pixel array 100 and controls the lighting device 12 to operate variably for 5~200 msec. The video signals are captured by the pixel array 100 during that time. According to that, each video frame is instantly captured, and brightness thereof is better. And a PSK method that is simple and has strong tolerance against noise is used in encoding.

When the signal transmitted from the coding circuit 120 is "1", the switching circuit 130 applies+voltage to the first output line 16a and grounds the second output line 16b. When the signal transmitted from the coding circuit 120 is "0", the switching circuit 130 grounds the first output line 16a and applies a+voltage to the second output line 16b. As described-above, since the present invention transmits a signal using not the voltage size but the voltage polarity, it can be stronger to noise.

The current limiting circuit 140 serves to prevent a current more than 5 mA from flowing through the human body. In the embodiment of the present invention, the current limiting circuit 140 is implemented by serially connecting resistors to the two output lines 16 of the switching circuit 130 respectively. For example, assume that when a power voltage is 3 V the current limiting circuit 140 comprises resistors of 300 ohms serially connected to the two output lines respectively. In this case, although the transmitting electrode has a substantial short circuit because of very small resistance of the human body, current flowing through the human body does not exceed 5 mA. In addition, by connecting a capacitor to each resistance in parallel, it is possible to remove a high frequency component of the signal transmitted to the human body and perform electric matching with the human body, so that signal-transmitting performance can be improved.

The signal passing the current limiting circuit 140 is applied to the two transmitting electrodes 11 and is transmitted to the outside of the human body through the human body. In the conventional frequency communication method, a high frequency signal of several hundred MHz is required, however, in the present invention, a video signal captured by the capsule type endoscope can be transmitted to the outside of the human body with a low frequency signal of 10 MHz.

Industrial Applicability

Since the present invention uses a low frequency and current instead of a high frequency through antenna when communicating with sensor in the human body, it reduces power consumption and attenuation in human body, has no effect on external interference and cause no damage to the human body. In addition, since the invention transmits a signal using voltage polarity, it is strong to noise, and accordingly receiving sensitivity is superior.

In addition, the sensor in accordance with the present invention does not need a radio transmitter and antenna, and also does not need an additional memory because it processes video signals sequentially along the passage of time, so that a small-sized and low-priced capsule type endoscope can be provided.

The invention claimed is:

1. A method for transmitting a signal from a sensor put in a human body to the outside of the human body, the method comprising:
generating electric potential difference between transmitting electrodes installed on the surface of the sensor, the sensor capable of being ingested and capable of traveling autonomously within the human body;
switching the transmitting electrodes according to information to be transmitted, to create:
a first state, wherein a first transmitting electrode has a higher electric potential and a second transmitting electrode has a lower electric potential; and
a second state, wherein the first transmitting electrode has a lower electric potential and the second transmitting electrode has a higher electric potential;
supplying a conduction current from the first transmitting electrode having the higher electric potential to an inside of the human body to flow a current through a surface of the human body back into the inside of the human body, and sinking the current to the second transmitting electrode having lower electric potential;
inducing a voltage between receiving electrodes installed on the surface of the human body by the current flowing through the surface of the human body; and
controlling an amount of the conduction current flowing through the body,
wherein during the first state, a positive voltage is applied to the first transmitting electrode and the second transmitting electrode is grounded, and
wherein during the second state, the first transmitting electrode is grounded and the positive voltage is applied to the second transmitting electrode.

2. The method of claim 1, wherein the generating the electric potential difference comprises controlling an output of the transmitting electrodes to be transmitted to an outside of the human body by a switching circuit.

3. The method of claim 2, wherein the controlling of the output of the transmitting electrodes comprises switching an input signal to the transmitting electrodes by the switching circuit, so that:
the first state is represented when the first transmitting electrode has a higher electric potential and the second transmitting electrode has a lower electric potential; and
the second state is represented when first transmitting electrode has a lower electric potential and second transmitting electrode has a higher electric potential.

4. The method of claim 3, further comprising supplying the conduction current in a digital form.

5. The method of claim 4, further comprising inducing a digital voltage between the receiving electrodes installed on the surface of the human body by the conduction current flowing through the surface of the human body.

6. A system for data communication in a human body, the system comprising:
a sensor, which is put in the human body, and having transmitting electrodes installed on a surface of the sensor configured to be electrically isolated and configured to generate electric potential difference, the sensor capable of being ingested and capable of traveling autonomously within the human body,
a coding circuit located in the sensor;
a switching circuit that switches, based on an output from the coding circuit, the transmitting electrodes, to create:
a first state, wherein a first transmitting electrode has a higher electric potential and a second transmitting electrode has a lower electric potential; and
a second state, wherein the first transmitting electrode has a lower electric potential and the second transmitting electrode has a higher electric potential;
a receiver installed on a surface of the human body to receive a conduction current generated by the electric potential difference through the human body; and a circuit to control an amount of the conduction current flowing through the body, wherein during the first state, the switching circuit applies a positive voltage to the first transmitting electrode and grounds the second transmitting electrode, and wherein during the second state, the switching circuit grounds the first transmitting electrode and applies the positive voltage to the second transmitting electrode.

7. The system of claim 6, wherein the transmitting electrodes are installed on the surface of the sensor and are configured to be electrically isolated.

8. The system of claim 7, wherein the transmitting electrodes are three-dimensionally formed.

9. The system of claim 8, wherein the sensor includes a first electrode and a second electrode which surround both ends of the sensor.

10. The system of claim 8, wherein the sensor includes a first electrode surrounding an end of the sensor and a second electrode covering an other end of the sensor as a band shape.

11. The system of claim 8, wherein the sensor includes a first electrode and a second electrode respectively covering both ends of the sensor as a band shape.

12. The system of claim 8, wherein the sensor includes a first electrode and a second electrode symmetrically formed along a longer axis of the sensor.

13. The system of claim 6, wherein the transmitting electrodes are electrically connected with an internal circuit of the sensor to receive an electric signal generated from the internal circuit.

14. The system of claim 6, wherein the surface of the sensor for isolating of the transmitting electrodes is made of one of peek, polyethylene and polypropylene.

15. The system of claim 14, wherein the surface of the sensor for isolating of the transmitting electrodes is coated with Parylene.

16. The system of claim 6, wherein the surface of the sensor is made of a conductive material harmless to the human body.

17. The system of claim 16, wherein the conductive material comprises SUS316L or gold.

18. The system of claim 6, wherein the sensor further comprises a current limiting circuit that is located between the switching circuit and the transmitting electrodes.

19. A method for transmitting a signal from a capsule type endoscope put in a human body to an outside of the human body, the method comprising:

generating electric potential difference between a first transmitting electrode and a second transmitting electrode installed on a surface of a capsule type endoscope, the capsule type endoscope capable of being ingested and capable of traveling autonomously within the human body;

switching the transmitting electrodes according to information to be transmitted, to create:

a first state, wherein the first transmitting electrode has a higher electric potential and the second transmitting electrode has a lower electric potential; and a second state, wherein the first transmitting electrode has a lower electric potential and the second transmitting electrode has a higher electric potential;

supplying a conduction current from the first transmitting electrode having a higher electric potential to an inside of the human body to flow a current through a surface of the human body back into the inside of the human body and sinking the current to the second transmitting electrode having the lower electric potential;

inducing a voltage between receiving electrodes installed on the surface of the human body by the current flowing through the surface of the human body; and controlling an amount of the conduction current flowing through the body, wherein the capsule type endoscope makes a current flow from one transmitting electrode to the other transmitting electrode when a signal to be transmitted is a digital signal "1" and makes a current flow from the other transmitting electrode to one transmitting electrode when a signal to be transmitted is a digital signal "0."

20. The method of claim 19, wherein a size of the current is limited by connecting resistance serially to the transmitting electrode respectively.

21. The method of claim 20, wherein a capacitor is connected to each resistance in parallel.

* * * * *